(12) United States Patent
Fischer

(10) Patent No.: US 8,623,016 B2
(45) Date of Patent: Jan. 7, 2014

(54) ELECTROSURGICAL INSTRUMENT

(75) Inventor: Klaus Fischer, Nagold (DE)

(73) Assignee: Erbe Elektromedizin GmbH, Tübingen (DE)

( * ) Notice: Subject to any disclaimer, the term of this patent is extended or adjusted under 35 U.S.C. 154(b) by 1306 days.

(21) Appl. No.: 11/631,042

(22) PCT Filed: May 25, 2005

(86) PCT No.: PCT/EP2005/005680
§ 371 (c)(1),
(2), (4) Date: Dec. 28, 2006

(87) PCT Pub. No.: WO2006/000280
PCT Pub. Date: Jan. 5, 2006

(65) Prior Publication Data
US 2008/0045944 A1 Feb. 21, 2008

(30) Foreign Application Priority Data
Jun. 28, 2004 (DE) .......................... 10 2004 031 141

(51) Int. Cl.
*A61B 18/18* (2006.01)
(52) U.S. Cl.
USPC .................. 606/51; 606/50; 606/52
(58) Field of Classification Search
USPC .......................... 606/48, 51, 52, 46
See application file for complete search history.

(56) References Cited

U.S. PATENT DOCUMENTS

| | | | |
|---|---|---|---|
| 5,891,142 A | 4/1999 | Eggers et al. | |
| 5,954,720 A | 9/1999 | Wilson et al. | |
| 6,273,887 B1 | 8/2001 | Yamauchi et al. | |
| 6,364,879 B1 | 4/2002 | Chen et al. | |
| 6,679,882 B1 * | 1/2004 | Kornerup | 606/51 |
| 6,736,813 B2 | 5/2004 | Yamauchi et al. | |
| 2001/0037109 A1 * | 11/2001 | Yamauchi et al. | 606/48 |
| 2003/0109876 A1 * | 6/2003 | Yamauchi | 606/48 |

FOREIGN PATENT DOCUMENTS

| | | | |
|---|---|---|---|
| CN | 1976642 | 6/2007 | |
| DE | EP 0 797 959 | 3/2003 | |
| EP | 0986990 A1 | 3/2000 | |
| JP | 2000-102545 A | 4/2000 | |
| JP | 2002-078717 A | 3/2002 | |
| JP | 2003-116669 A | 4/2003 | |
| JP | 2004-516043 | 6/2004 | |
| WO | WO-02/07627 A1 | 1/2002 | |
| WO | WO 2004032777 A1 * | 4/2004 | A61B 18/14 |

* cited by examiner

*Primary Examiner* — Linda Dvorak
*Assistant Examiner* — Jaymi Della
(74) *Attorney, Agent, or Firm* — Dickstein Shapiro LLP

(57) ABSTRACT

The invention concerns an electrosurgical instrument comprising two articulated branches, which can be actuated in the manner of a squeezing tool. The instrument further comprises electrode parts at the distal ends of the branches for grasping tissue and for conducting a coagulating current through the tissue in order to cause it to coagulate as well as current-supplying devices for supplying the coagulating current to the electrode parts from an HF generator. At least one device for preventing a short circuit is arranged and configured on the electrode parts in such a way that the electrode parts are unable to touch.

10 Claims, 4 Drawing Sheets

ELECTROSURGICAL INSTRUMENT

CROSS-REFERENCE TO RELATED APPLICATIONS

This application is related to and claims priority from German Patent Application No. DE 10 2004 031 141.2, filed on Jun. 28, 2004, the entirety of which is incorporated herein by reference.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention concerns an electrosurgical instrument.

BACKGROUND OF THE INVENTION

Electrosurgical instruments have been used for many years in high-frequency surgery to coagulate or cut biological tissue. With coagulation, a high-frequency current is passed through the tissue being treated, causing it to alter due to protein coagulation and dehydration. Here, the tissue constricts in such a way that the vessels occlude and bleeding is staunched. A high current density is required for a cutting procedure, the effect being that explosive vaporisation of the tissue fluid and tearing of the cellular membranes completely cut the tissue in two.

The use of bipolar instruments is gaining in importance more and more, since lower current strengths than with monopolar instruments are required. It is particularly advantageous that the direction of current between the electrode parts of bipolar instruments can be calculated and does not proceed any distance through the body of the patient.

Bipolar instruments have two articulated squeezing parts and gripping devices are provided at their proximal ends for handling the squeezing parts. At the distal ends of the squeezing parts, there are electrode parts for grasping tissue and for conducting a coagulating current through the tissue. A voltage produced by a HF generator, and the HF current which this provides, is conducted via current-supplying devices to the electrode parts of the bipolar instrument. To prevent a short circuit upon contact of the two electrode parts, the known instruments have a device for preventing a short circuit accommodated on the branches, whereby the electrode parts are always spaced apart when the instrument is closed.

The problem with the known devices for preventing a short circuit is that they only indirectly define the space between the electrode parts, because they are accommodated away from the electrode parts. Thus, the aspect ratios of the branches, for example, need to be taken into account to determine the appropriate space. This makes the adjustment of space and required HF voltage considerably difficult.

BRIEF SUMMARY OF THE INVENTION

It is therefore the object of the invention to further construct an electrosurgical instrument of the type specified at the start so that it is possible to adjust the space between the electrode parts to the required HF voltage.

According to the invention there is provided an electrosurgical instrument comprising consisting of two articulated branches, which are actuated in the manner of a squeezing tool. The instrument further comprises electrode parts at the distal ends of the branches for grasping tissue and for conducting a coagulating current through the tissue to cause it to coagulate as well as current-supplying devices for supplying the coagulating current to the electrode parts from a HF generator. At least one device for preventing a short circuit is arranged and configured on the electrode parts in such a way that the electrode parts are unable to touch.

Hence, in the present invention the device for preventing a short circuit is now arranged directly at the place where the effective space must be, that is, between the electrode parts. At the same time, coagulation is not prevented, because the tissue is also able to coagulate at a point of contact between tissue and device due to thermal conduction. To this extent, any sparking between the electrode parts can be reliably avoided with a coagulating procedure.

In one preferred embodiment, the device for preventing a short circuit has a distance element provided as an insulating section on at least one electrode part. Thus the short circuit between the electrode parts is prevented by the distance element, should these touch.

In another preferred embodiment, adjoining the insulating section, at least one initial cutting section is arranged on at least one of the electrode parts, in particular configured with a reduced space from the opposite electrode relative to the coagulating electrodes, in such a way that an arc for cutting through the tissue is produced from the initial cutting section with any increase in the voltage of the coagulating current. The cutting section is preferably arranged on the electrode part as an area that tapers in relation to the electrode part and protrudes from this. The electrode part will then have an explicit coagulating section beside the cutting section. The electrode part forming the coagulating section and the cutting section may, during a coagulating procedure, operate as a coagulating electrode over its entire surface area, i.e. both over the surface area of the coagulating section and over the surface area of the cutting section, whereas the tapered cutting section is available solely for a subsequent cutting procedure.

The cutting section guarantees that the arc is only produced here, whereas a disruptive discharge to the opposite electrode cannot occur on the rest of the electrode section as a result of too great a space between the electrode parts. Thus one and the same instrument can be used to both coagulate and cut, and a change of instrument can be avoided to the benefit of an uninterrupted operation.

The distance element may be configured as both linear in shape and punctiform. The distance element that is linear in shape will then extend, for example, in the direction of the branch progression, concentrically arranged on the electrode part, over the entire electrode part and accordingly form an edge. Advantageously, in this way the steady formation of an arc is made possible and an even cut is guaranteed. A punctiform distance element is easy to manufacture, reliably prevents a short circuit occurring between the electrode parts and, as a result of thermal conduction, also guarantees safe coagulation at the point of contact between tissue and distance element. Several punctiform distance elements arranged on the corresponding electrode part, e.g. at the respective ends of the electrode part, reliably prevent a short circuit and affect neither the coagulating nor the cutting procedure.

Preferably, a second cutting section will be configured on the electrode part facing the electrode part with the insulating section. This is particularly advantageous if the insulating section facing the second cutting section is arranged directly on the electrode part so that the electrode part does not have an explicit initial cutting section. In this embodiment, the insulating section is preferably smaller than the opposite cutting section, with the result that an arc can be formed around peripheral areas of the insulating section toward the opposite cutting section. This enables a precise cut to be achieved.

Alternatively, it is possible to configure the cutting section on both opposing electrode parts. Thus the area for the arc formation and the cutting progression are extremely precisely defined.

Preferably, the device for preventing a short circuit has at least one insulating section which is formed within an electrode part. A distance element provided as a cutting section is then configured on the electrode part facing the insulating section. The cutting section is arranged in such a way that it only comes into contact with the insulating section when the branches are brought together. Advantageously, a precise cut is also provided for here since the arc is formed between the incorporated section and the cutting section. The insulating section with this embodiment is protected from jolts or similar mechanical strains and essentially from the arc also.

The insulating section in this embodiment may be configured so as to be flush with an electrode surface of the electrode part that has the insulating section. This allows the electrode part to be cleaned simply and safely after treatment.

Alternatively, it is possible to arrange the insulating section so that it is sunk in the corresponding electrode part, with the result that the electrode part has a recess. The cutting section configured on the opposite electrode part can thus be at least partially lowered into the recess so that an arc can form inside the recess toward the cutting section during the cutting procedure. Surrounding tissue is thus protected from burning, while at the same time a precise cutting line can be defined.

In one preferred embodiment, the insulating section is symmetrically arranged toward the initial cutting section and/or second cutting section on the respective electrode parts. A symmetrical arrangement of the cooperating sections guarantees a uniformly developing arc on peripheral areas of the distance element, making for an even cutting progression.

One possible embodiment provides for the distance element being configured in such a way that mechanical cutting can be carried out. Preferably, the distance element will then have a cutting edge which lends itself to mechanical cutting. With appropriate exertion on the part of the surgeon, the tissue can then be cut through completely following a coagulating procedure and without having to change instrument. This allows an especially soft treatment of the tissue to be achieved.

In one preferred embodiment the cutting section is configured as an edge with an essentially triangular cross-section on at least one electrode part. A triangular cross-section allows for the successive transition from one large surface area of the electrode part to its edge-shaped tapering. The smooth transition is especially suited to using the entire electrode part as a coagulating electrode where there is sufficient tissue thickness, because the entire surface area and the tissue can be brought into contact with each other.

Advantageously, the cutting section is configured as an edge with an essentially rounded or circular cross-section on at least one electrode part, as is illustrated in FIG. 8, for example. On one transition between the explicit coagulating section and the cutting section, the preference is to configure the cutting section in a truncated manner so that a secure anchorage of the cutting section to the corresponding electrode part is guaranteed. With this embodiment there is a relatively large electrode surface available for the coagulating procedure, whereas the cutting section configured as an edge is hardly of any consequence where there is sufficient tissue thickness. At an advanced stage of an operation, on the other hand, and with sufficient proximity of the opposite electrode parts of the electrosurgical instrument, the edge-shaped configuration of the cutting section allows the current density to be increased in such a way that a cutting procedure is possible.

Preferably, the insulating section is constructed from material that is resistant to arc erosion. Thus, reliable resistance to abrasion from the arc is provided.

In one preferred embodiment the insulating section consists of a ceramic material. Advantageously, ceramics have a high degree of resistance to corrosion and a high degree of resistance to abrasion from the arc and also to mechanical strain.

Embodiments of the invention will now be described by way of examples with reference to the accompanying drawings.

DETAILED DESCRIPTION OF THE INVENTION

Figure 1A:
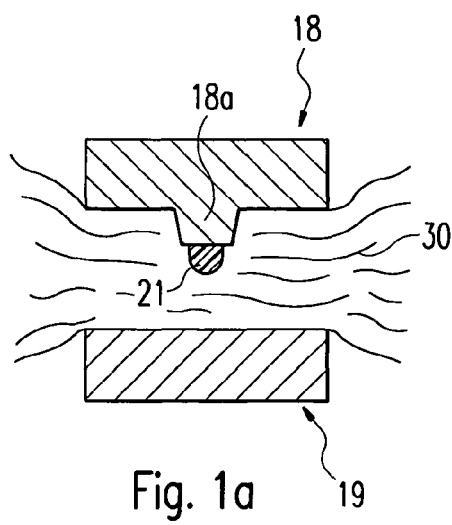
FIG. 1*a* is a cross-section of a schematically represented electrode arrangement in a first embodiment during a coagulation phase.

In the following description, the same reference numerals are used for the same and similarly working parts.

FIG. 1*a* depicts a front elevation as a cross-section of an electrode arrangement during a coagulation phase in a first embodiment. Represented here are two opposite electrode parts 18, 19, wherein one electrode part 18 has a cutting section or a cutting portion 18*a* and an insulating section or an insulating portion 21 configured as a distance element. In this embodiment, the distance element forms a device 20 for preventing a short circuit. Treated tissue 30 is clamped between the electrodes.

The insulating section 21 prevents an unwanted short circuit between the electrode parts 18, 19 when the branches 11, 12 are brought together and may be configured as both linear in shape and punctiform. The distance element that is linear in shape will then extend, for example, in the direction of the branch progression, concentrically arranged on the electrode part, over the entire electrode part and accordingly form an edge. Advantageously, the steady formation of an arc is thus made possible and an even cut is guaranteed. A punctiform distance element is easy to manufacture, reliably prevents a short circuit occurring between the electrode parts and, as a result of thermal conduction, also guarantees safe coagulation at the point of contact between tissue and distance element. Several punctiform distance elements arranged on the corresponding electrode part, e.g. at the respective ends of the electrode part, reliably prevent a short circuit and affect neither the coagulating nor the cutting procedure. The cutting section 18a is in any event configured as linear in shape.

Besides preventing a short circuit, the section 21 defines a thickness of the tissue 30 that remains after the coagulation phase, because it prevents an arc forming prematurely with any pre-set coagulating voltage due to too small a space between the electrode parts 18, 19.

Figure 1B:
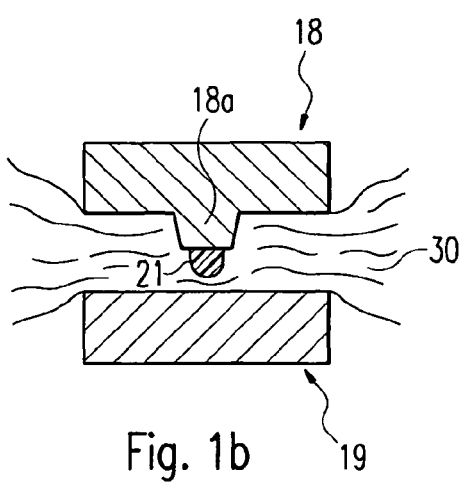
FIG. 1*b* shows the electrode arrangement shown in FIG. 1*a* at the end of the coagulation phase.

FIG. 1b depicts the electrode arrangement according to FIG. 1a, although here the end of the coagulation is represented. According to FIGS. 1a and 1b a coagulating current flows over an entire surface of the electrode parts 18, 18a, 19, with the effect that the interposed tissue 30 is coagulated. As a result of thermal conduction the tissue 30 is coagulated under the insulating section 21.

Figure 1C:
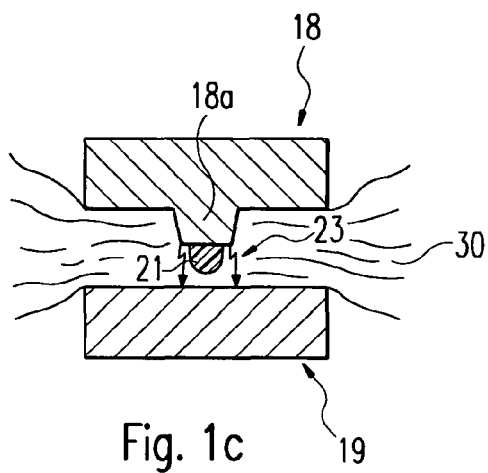
FIG. 1*c* shows the electrode arrangement shown in FIG. 1*a* during a cutting phase.

FIG. 1c depicts the electrode arrangement described above during a cutting phase. At the end of the coagulation phase, a HF voltage required for the electrosurgical treatment is slightly increased, with the result that between the cutting section 18a and the opposite electrode part 19 the arc 23 is formed, which now cuts through the already coagulated tissue 30.

The cutting section 18a is preferably arranged on the electrode part 18 as an area that tapers in relation to the electrode part 18 and protrudes from this. The electrode part 18 will then consist of an explicit coagulating section beside the cutting section 18a. The electrode part 18 forming the coagulating section and the cutting section 18a may, during a coagulating procedure, operate as a coagulating electrode over its entire surface area, i.e. both over the surface area of the coagulating section and over the surface area of the cutting section 18a, whereas the tapered cutting section 18a is available solely for a subsequent cutting procedure.

The height of the insulating section 21 and thus the space from the cutting section 18a and opposite electrode part 19 and the HF voltage required for cutting are adjusted to each other. The formation of the arc 23 outside the cutting section 18a, that is, on the remaining areas of the electrode part 18, is thus avoided.

Because of the electrode arrangement just described, one and the same instrument can be used to both coagulate and cut, and a change of instrument can be avoided to the benefit of an uninterrupted operation.

Figure 2:
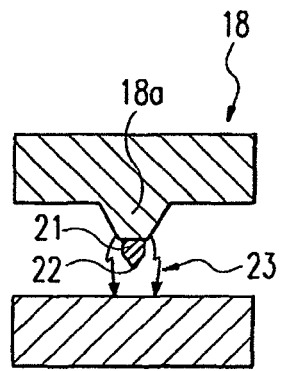
FIG. 2 is a cross-section of a schematically represented electrode arrangement in a second embodiment.

In FIG. 2 a front elevation as a cross-section of an electrode arrangement is represented in a second embodiment. Tissue clamped between the electrode parts during a treatment is not represented in this embodiment for the benefit of better clarity. The same applies, moreover, to FIG. 3 to 6. The arrangement differs from the one represented in FIG. 1a to 1c in that a cutting section 18a is configured as an edge with a triangular cross-section. Because of the successive transition from one large surface area of the electrode part 18 to its edge-shaped tapering, this embodiment is especially suited to using the entire electrode part 18 as a coagulating electrode where there is sufficient tissue thickness, because the entire surface area and the tissue can be brought into contact with each other. With a suitable HF voltage, an arc 23 is formed between the cutting section 18a and an opposed electrode part 19.

The insulating section 21 has in this instance a tapered shape to also facilitate mechanical cutting where necessary, that is, the distance element has an explicit cutting edge 22.

With appropriate exertion on the part of the surgeon, the tissue can then be cut through completely following a coagulating procedure and without having to change instrument. This makes for an especially gentle treatment of the tissue without the use of an arc.

Figure 3:
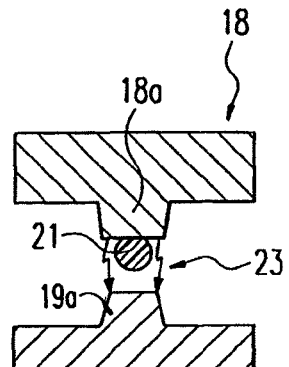
FIG. 3 is a cross-section of a schematically represented electrode arrangement in a third embodiment.

FIG. 3 depicts a front elevation as a cross-section of an electrode arrangement in a third embodiment. Here both a cutting section 18a is configured on an electrode part 18 and a cutting section 19a is configured on an electrode part 19. An insulating section 21 is arranged directly below the cutting section 18a and symmetrically to the cutting sections 18a, 19a. A symmetric arrangement of the cooperating sections 18a, 21, 19a guarantees a uniformly developing arc 23 on peripheral areas of the insulating section 21, making for an even cutting progression. The insulating section 21 functioning as a distance element is smaller than the cutting sections 18a, 19a, so as not to prevent the arc 23 from forming. Because of the narrow cutting sections 18a, 19a accommodated on the electrode parts 18, 19, the cutting progression can be extremely precisely defined.

Figure 4:
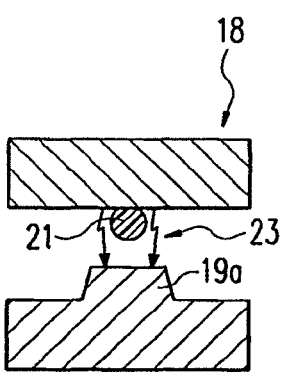
FIG. 4 is a cross-section of a schematically represented electrode arrangement in a fourth embodiment.

An extremely simple embodiment of an electrode arrangement is depicted in FIG. 4. Here an electrode part 19 only has one cutting section 19a, whereas on an electrode part 18 facing the electrode part 19 there is only an insulating section 21 configured. Because the arc 23 forms in the direction of the cutting section 19a, this embodiment allows an exact cutting line to be defined in an especially easy way.

Figure 5:
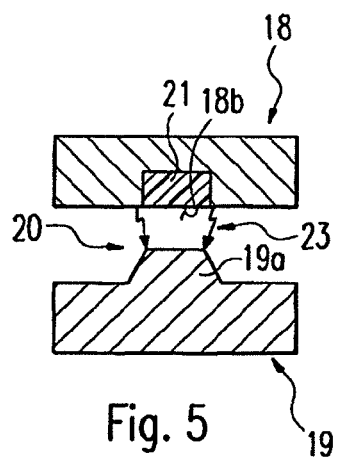
FIG. 5 is a cross-section of a schematically represented electrode arrangement in a fifth embodiment.

FIG. 5 depicts a front elevation as a cross-section of an electrode arrangement where an electrode part 18 has an insulating section 21 configured within the electrode part 18, wherein the insulating section 21 terminates flush with an electrode surface 18b. A second cutting section 19a is provided as a distance element on an opposing electrode part 19. The insulating section 21 and the cutting section 19a operate in this embodiment as a device 20 for preventing a short circuit. Advantageously, a precise cut is also provided for here since the arc 23 is formed between the incorporated section 21 and the cutting section 19a. The insulating section 21 with this embodiment is protected from jolts or similar mechanical strains and essentially from the arc 23 also.

Figure 6:
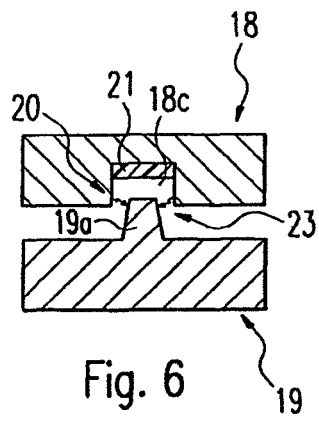
FIG. 6 is a cross-section of a schematically represented electrode arrangement in a sixth embodiment.

FIG. 6 depicts a similar configuration of an electrode arrangement as represented in FIG. 5. An insulating section 21 is configured here, however, to be sunk in a corresponding electrode part 18, so that a recess 18c is formed on the electrode part 18. A cutting section 19a configured on an opposing electrode part 19 can be at least partially lowered into the recess 18c, so that an arc 23 can form inside the recess 18c toward the cutting section 19a during the cutting procedure. Surrounding tissue is thus protected from burning, while at the same time a precise cutting line can be defined.

In this embodiment, too, the cutting section 19a may be configured with an explicit cutting edge, allowing the tissue to be cut through mechanically.

Figure 7:
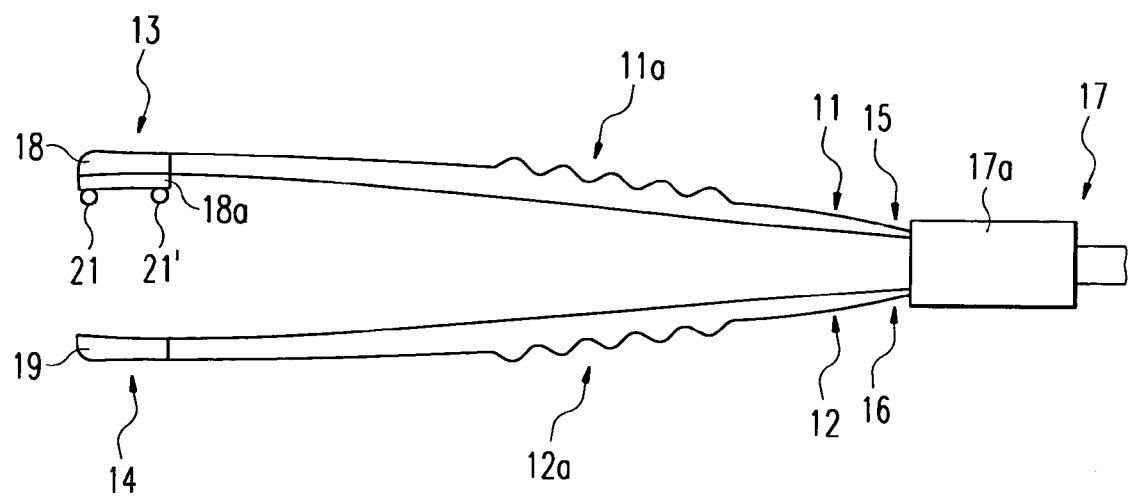
FIG. 7 is a side elevation of a schematically represented electrosurgical instrument with an electrode arrangement according to the invention.
Figure 8:
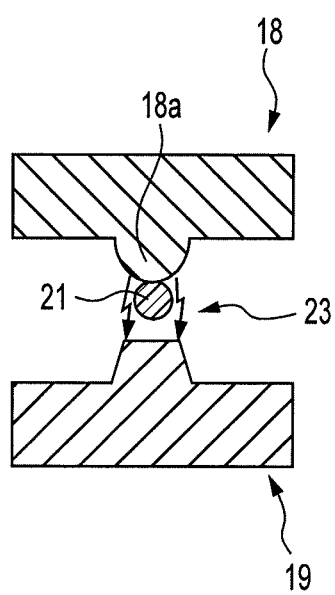
FIG. 8 is a cross-section of a schematically represented electrode arrangement in a further embodiment.

FIG. 7 depicts a fully illustrated electrosurgical instrument 10 with an electrode arrangement according to the invention. In the illustration the reference numerals 11 and 12 identify two branches of the electrosurgical instrument 10. These branches 11, 12 have ends 13, 14 fitted with electrode parts 18, 19, wherein the electrode parts 18, 19 face each other. With the aid of the electrode parts 18, 19, it is possible to grasp a vessel, for example, and to coagulate or cut this by supplying a high-frequency current. In addition, gripping parts 11a, 12a are provided which are attached to respective proximal ends 15, 16 of the branches 11, 12. The proximal ends 15, 16 of the squeezing parts 11, 12 end in a connecting element 17a of current-supplying devices 17. The current-supplying devices 17 serve to connect the electrosurgical instrument 10 to a HF generator (not represented), which produces a HF voltage, so that a HF current may be supplied to the electrode parts 18, 19 by, for example, electrical leads (not depicted) running through the instrument 10.

An edge-shaped cutting section 18a is configured on the electrode part 18. This has two insulating sections 21, 21' configured as two punctiform distance elements. The distance elements arranged at the respective ends of the electrode part 18 or on the cutting section 18a reliably prevent a short circuit and affect neither the coagulating nor the cutting procedure.

To achieve a high degree of resistance of the insulating section to an arc, the section is preferably constructed from material that is resistant to arc erosion. A high degree of resistance to abrasion is provided in particular by the use of ceramic materials.

LIST OF REFERENCE NUMERALS

10 Electrosurgical instrument
11 Squeezing part, branch
11a Gripping part
12 Squeezing part, branch
12a Gripping part
13 Distal end
14 Distal end
15 Proximal end
16 Proximal end
17 Current-supplying devices
17a Connecting element
18 Electrode part
18a Cutting section
18b Electrode surface
18c Recess
19 Electrode part
19a Cutting section
20 Device for preventing a short circuit
21, 21' Insulating section
22 Cutting edge
23 Arc
30 Tissue

The invention claimed is:

1. An electrosurgical instrument comprising:
   two articulated branches, each with a distal end, which are actuated in the manner of a squeezing tool;
   electrode parts comprising a first electrode part and an opposing electrode part, the first electrode part being at the distal end of one of the two articulated branches and the opposing electrode part being at the distal end of the other of the two articulated branches, the electrode parts being adapted to grasp tissue and to conduct a coagulation current through the tissue in order to cause it to coagulate or a cutting current in order to cause it to cut the tissue;
   current-supplying devices adapted to supply said coagulation and cutting currents to the first electrode part and the opposing electrode part from a high-frequency (HF) generator; and
   at least one device for preventing a short circuit which is configured on said electrode parts and arranged such that the first electrode part and the opposing electrode part are unable to touch one another, wherein
   the at least one device for preventing a short circuit comprises at least one insulating region forming part of a first distance element, and wherein
   the first electrode part or the opposing electrode part comprises a coagulation section and a cutting section protruding from the coagulation section, each of the coagulation section and the cutting section forming a surface area, wherein the surface areas of the coagulation section and the cutting section serve as a coagulating electrode, whereas the surface area of the cutting section but not the surface area of the coagulation section is available for a cutting procedure in such a way that an arc for cutting through the tissue is produced from the cutting section, and wherein the cutting section defines an edge having a substantially trapezoidal cross-section on at least one of the first electrode part or the opposing electrode part;
   the at least one insulating region is arranged in a projecting manner on the cutting section such that the at least one insulating region is arranged between the cutting section and the opposing electrode part if the two articulated branches are brought together, wherein said cutting section is symmetrical about said at least one insulating region, and wherein the at least one insulating region is smaller than the cutting section so as not to prevent the arc from forming, and wherein a height of the first distance element determines a distance between the cutting section and the opposing electrode part when the two articulated branches are in a closed position;
   the at least one device for preventing a short circuit comprises the at least one insulating region, which is arranged on one of the electrode parts, and a second distance element adapted as a second cutting section, which is configured on the opposing electrode part facing the at least one insulating region and which is adapted such that, when the two articulated branches are squeezed together, the second cutting section only touches the at least one insulating region.

2. An electrosurgical instrument according to claim 1, wherein the cutting section includes an initial cutting section that adjoins the at least one insulating region and is arranged such that, with any increase in a voltage of the coagulation or cutting currents, the arc for cutting through the tissue is produced from the initial cutting section.

3. An electrosurgical instrument according to claim 1, wherein said at least one insulating region is arranged symmetrically to at least one of said cutting section on the first electrode part and said second cutting section on the opposing electrode part.

4. An electrosurgical instrument according to claim 1, wherein said first distance element is adapted to enable mechanical cutting to be carried out.

5. Electrosurgical instrument according to claim 2, wherein said cutting section defines an edge with a rounded profile on at least one of said electrode parts.

6. An electrosurgical instrument according to claim 1, wherein said at least one insulating region is comprised of a material resistant to arc erosion.

7. An electrosurgical instrument according to claim 1, wherein said at least one insulating region is comprised of a ceramic material.

8. An electrosurgical instrument according to claim 1, wherein said second cutting section is symmetrical about said at least one insulating region when said second cutting section touches said at least one insulating region.

9. An electrosurgical instrument according to claim 1, wherein said first and second distance elements are adapted to enable mechanical cutting to be carried out.

10. Electrosurgical instrument according to claim 1, wherein said cutting section defines an edge with a rounded profile on at least one of said electrode parts.

* * * * *

UNITED STATES PATENT AND TRADEMARK OFFICE
CERTIFICATE OF CORRECTION

PATENT NO. : 8,623,016 B2
APPLICATION NO. : 11/631042
DATED : January 7, 2014
INVENTOR(S) : Klaus Fischer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1461 days.

Signed and Sealed this
Twenty-second Day of September, 2015

Michelle K. Lee
*Director of the United States Patent and Trademark Office*